United States Patent
Eggers et al.

(10) Patent No.: US 6,312,428 B1
(45) Date of Patent: Nov. 6, 2001

(54) METHODS AND APPARATUS FOR THERAPEUTIC CAUTERIZATION OF PREDETERMINED VOLUMES OF BIOLOGICAL TISSUE

(75) Inventors: Philip E. Eggers, Dublin, OH (US); Ascher Shmulewitz, Mercer Island, WA (US)

(73) Assignee: Neothermia Corporation, Menlo Park, CA (US)

( * ) Notice: Subject to any disclaimer, the term of this patent is extended or adjusted under 35 U.S.C. 154(b) by 0 days.

(21) Appl. No.: 09/351,991

(22) Filed: Jul. 12, 1999

Related U.S. Application Data

(63) Continuation-in-part of application No. 08/842,009, filed on Apr. 23, 1997, now Pat. No. 5,928,159, which is a continuation of application No. 08/887,663, filed on Jul. 3, 1997, now Pat. No. 5,947,964, which is a continuation of application No. 08/398,644, filed on Mar. 3, 1995, now Pat. No. 5,630,426.

(51) Int. Cl.$^7$ .................................................... A61B 18/18

(52) U.S. Cl. ............................... 606/41; 606/48; 606/50; 607/101

(58) Field of Search ...................... 606/29, 31, 40–42, 606/45–50; 607/98–102

(56) References Cited

U.S. PATENT DOCUMENTS

| | | |
|---|---|---|
| Re. 34,421 | 10/1993 | Parker et al. . |
| 4,016,886 | 4/1977 | Doss et al. . |
| 4,121,592 | 10/1978 | Whalley . |
| 4,140,109 | 2/1979 | Savic et al. . |
| 4,291,708 | 9/1981 | Frei et al. . |
| 4,458,694 | 7/1984 | Sollish et al. . |
| 4,520,249 | 5/1985 | Czerlinski . |
| 4,658,836 | 4/1987 | Turner . |
| 4,674,499 | * 6/1987 | Pao . |
| 4,679,561 | 7/1987 | Doss . |
| 4,737,628 | 4/1988 | Lovoi . |
| 4,776,334 | 10/1988 | Prionas . |
| 4,805,616 | * 2/1989 | Pao . |
| 4,821,725 | 4/1989 | Azam et al. . |
| 4,846,196 | 7/1989 | Wiksell et al. . |
| 4,860,744 | 8/1989 | Johnson et al. . |
| 4,872,458 | 10/1989 | Kanehira et al. . |
| 4,919,138 | 4/1990 | Nordenstroöm . |

(List continued on next page.)

FOREIGN PATENT DOCUMENTS

| | | |
|---|---|---|
| 0 249 631 | 9/1989 | (DE) . |
| 39 30 451 | 3/1991 | (DE) . |

OTHER PUBLICATIONS

Savic, M. and Zacarian, S.A., "A New Impedance–Based Method for Controlled Cryosurgery of Malignant Tumors", *The Journal of Dermatologic Surgery and Oncology*, Nov./Dec. 1977, pp. 592–593.

Abele, J.S., et al., "Fine–Needle Aspiration of Palpable Breast Masses", *Arch. Surgery*, Jul. 1983, pp. 859–863.

Morimoto, T., et al., "Measurement of the Electrical Bio–Impedance of Breast Tumors", *European Surgery Research*, 1990, pp. 86–92.

Primary Examiner—Roy Gibson
(74) Attorney, Agent, or Firm—Mueller and Smith, LPA

(57) ABSTRACT

Methods and apparatus are provided for cauterizing predetermined volumes of abnormal biological tissue using a user selectable or adjustable energy applicator including two or more electrodes having electrode parameters configured cause cauterization of predetermined volumes when operated in a bipolar mode. The energy applicators are employed with a control device that couples the energy applicators to a power source and includes circuitry for interrupting activation of the energy applicator when the current between the two or more electrodes decreases more than a predetermined amount from the current sensed upon initial activation of the energy applicator.

36 Claims, 8 Drawing Sheets

U.S. PATENT DOCUMENTS

| | | |
|---|---|---|
| 4,920,978 | 5/1990 | Colvin . |
| 4,979,518 | 12/1990 | Itoh et al. . |
| 5,069,223 | 12/1991 | McRae . |
| 5,085,659 * | 2/1992 | Rydell .................................. 606/47 |
| 5,117,828 * | 6/1992 | Metzger et al. . |
| 5,122,137 | 6/1992 | Lennox . |
| 5,125,928 * | 6/1992 | Parins et al. ......................... 606/48 |
| 5,143,079 | 9/1992 | Frei et al. . |
| 5,251,645 | 10/1993 | Fenn . |
| 5,284,144 | 2/1994 | Delannoy et al. . |
| 5,330,470 * | 7/1994 | Hagen .................................. 606/42 |
| 5,383,874 * | 1/1995 | Jackson et al. ....................... 606/1 |
| 5,429,636 * | 7/1995 | Shikhman et al. ................... 606/41 |
| 5,458,597 | 10/1995 | Edwards et al. . |
| 5,472,441 | 12/1995 | Edwards et al. . |
| 5,486,161 | 1/1996 | Lax et al. . |
| 5,507,743 | 4/1996 | Edwards et al. . |
| 5,514,130 * | 5/1996 | Baker ................................... 606/41 |
| 5,536,267 | 7/1996 | Edwards et al. . |
| 5,599,345 | 2/1997 | Edwards et al. . |
| 5,599,346 | 2/1997 | Edwards et al. . |
| 5,861,002 * | 1/1999 | Desai ................................... 606/210 |

\* cited by examiner

METHODS AND APPARATUS FOR THERAPEUTIC CAUTERIZATION OF PREDETERMINED VOLUMES OF BIOLOGICAL TISSUE

RELATED APPLICATION DATA

This application is a continuation-in-part of U.S. patent application Ser. No. 08/842,009, filed Apr. 23, 1997, entitled APPARATUS AND METHOD FOR CHARACTERIZATION AND TREATMENT OF TUMORS, now U.S. Pat. No. 5,928,159 which is a continuation of U.S. patent application Ser. No. 08/398,644, filed Mar. 3, 1995, now U.S. Pat. No. 5,630,426, which is a continuation of Ser. No. 08/887,663 filed Jul. 3, 1997 now U.S. Pat. No. 5,947,964.

FIELD OF THE INVENTION

The present invention relates to apparatus and methods for in situ cauterization of biological tissue, and more particularly, for causing in situ necrosis of predetermined volumes of abnormal biological tissue, such as a malignant tumor.

BACKGROUND OF THE INVENTION

Apparatus and methods are known for inducing therapeutic hyperthermia in biological tissue by inductive, radiant, contact and joulean heating methods. Inductive methods, such as described in U.S. Pat. Nos. 5,251,645 and 4,679,561, heat a volume of tissue located within a body cavity by passing high frequency electromagnetic radiation through tissue positioned between two external electrodes located near or in contact with the patient's skin. Heating is achieved due to the interaction of the changing electromagnetic field within the tissue.

A drawback of the foregoing devices is that this approach to therapeutic hyperthermia heats a relatively large volume of tissue to elevated temperatures for extended periods of time. Typically, tissue is heated to temperatures of 6 to 10° C. above normal body temperature, with heating sources operating in a range from ultrasonic frequencies to microwave frequencies, for periods of 20 minutes or more to achieve a desired degree of necrosis. Such devices generally do not allow the volume of tissue to be well defined, resulting in either insufficient necrosis or excessive necrosis of surrounding healthy tissue. Consequently, diffuse and prolonged heating of tissue is often combined with chemotherapy or radiation therapy modalities.

Other previously known methods and apparatus include therapeutic heating of tissue using radiant sources as described in U.S. Pat. Nos. 5,284,144, 4,872,458, and 4,737,628. Radiant sources, such as lasers, produce localized heating of tissue, but do not permit the effected volume to be predetermined a priori.

In addition, contact heating methods and apparatus have been used for inducing therapeutic hyperthermia, such as described in U.S. Pat. Nos. 4,979,518, 4,860,744, 4,658,836, and 4,520,249. Contact heating methods are not well suited to heating a defined volume of material, such as a tumor mass, due to thermal gradient effects. For example, to heat a spherical volume of the tissue having a diameter of 2 cm to at least 60° C., a single heating element could be inserted along a diameter of the sphere. To raise the perimeter of the spherical volume to 60° C., the central regions must be raised to a higher temperature than the periphery to produce an adequate thermal gradient, as may be demonstrated using well-known thermal conduction equations.

A disadvantage of the often high thermal gradient across the spherical volume, depending on the tissue type and conductivity, is the unwanted evolution of steam, formation of eschar, and unwanted preferential heat transfer along the cannula support shaft, thereby detrimentally effecting healthy tissue outside the target region.

In order to overcome the foregoing limitations, dispersed contact heating methods also have been developed. For example, small spheres or wire segments of ferromagnetic alloys have been inserted into tumors in the brain and other tissue and heated to an auto-regulating temperature (i.e., the Curie temperature of the alloy) by an externally applied electromagnetic field. The resulting eddy current heating causes hyperthermia in the tissue immediately surrounding the small spheres or wire. segments.

Yet another approach to therapeutic hyperthermia, referred to as "electrosurgery," utilizes heating produced by the flow of electrical current through tissue, such as described in U.S. Pat. Nos. 5,599,346, 5,599,345, 5,486,161, 5,472,441, 5,458,597, 5,536,267, 5,507,743, 4,846,196, 4,121,592, and 4,016,886. Electrosurgery generally employs either a monopolar or bipolar modality. In the monopolar mode, electric current is conducted between a relatively small active electrode and a large return electrode located at a distance from the active electrode. Because in the monopolar mode the current density in tissue decreases as the square of the distance from the active electrode, it is difficult to obtain necrosis of a predetermined volume of tissue.

The bipolar mode of electrosurgical (joulean) heating, such as described in U.S. Pat. Nos. 5,122,137, 4,920,978, 4,919,138, and 4,821,725, involves passing current between tissue disposed between two electrodes of similar surface area. Like monopolar heating, however, the capability to heat tissue in a precise manner requires that the region of tissue to be exposed to therapeutic hyperthermia be accurately defined in terms of both location and dimensions.

In a further attempt to address the disadvantages of previously known devices, methods have been developed for monitoring and/or controlling the progress or extent of therapeutic heating (or cooling) of tissue. These techniques include measurement of tissue temperature in contact with the device, such as described in U.S. Pat. Nos. 5,122,137, 4,776,334, and 4,016,866, and direct measurement of tissue impedance, such as described in U.S. Pat. Nos. 5,069,223 and 4,140,109. A limitation of such previously known devices is the need for specially designed or dedicated control systems and/or power supplies capable of measuring the specific parameter of interest (e.g., temperature or electrical impedance). This requirement for specialized equipment often poses budgetary problems in health care institutions, thus limiting widespread acceptance of such devices.

Additionally, measurement of actual tissue impedance is complicated by the wide range of variation in the electrical properties of biological tissue depending on the fatty tissue content and vascularity of the tissue. Further, tissue temperature measurements may be influenced by the distance between the temperature sensor and the working surface of the device, often resulting in underestimation of temperatures for more distal regions of tissue. In particular, the use of electrosurgical heating methods can lead to tissue heating effects which may be several or tens of millimeters from the working surface, well beyond the range of a temperature sensor mounted near the working surface.

Another important limitation of previously known devices and methods is the necessity of an invasive procedure, following the biopsy procedure, to treat abnormal or diseased tissue. For example, breast tumors or other abnormal tissue masses may be first identified by palpation, radiography, thermography and/or ultrasonography. Once a tumor is detected, a biopsy needle is used to extract a tissue sample (under the guidance of radiographs, ultrasound and/or palpation), and the biopsy needle is withdrawn from the patient. If hyperthermic treatment is indicated, the patient is subsequently exposed to a separate procedure (often invasive) which may be hours, days, weeks or longer after the initial invasive needle biopsy procedure.

In view of the foregoing, it would therefore be desirable to provide methods and apparatus, for use with existing tumor imaging techniques, capable of applying therapeutic hyperthermia, in situ, to any tumor which may be identified using minimally invasive procedures.

It would further be desirable to provide methods and apparatus for effecting complete necrosis of an identified tumor mass of predetermined volume, with minimal damage to surrounding healthy tissue.

It also would be desirable to provide methods and apparatus for effecting treatment of a tumor in single procedure that achieves therapeutic hyperthetmia of a predetermined volume of tissue within a brief period of time (e.g., several seconds to tens of seconds).

It would still further be desirable to provide methods and apparatus for effecting the treatment of a tumor promptly after completion of a biopsy procedure, thus permitting utilization of the vectoring biopsy needle guide cannula and/or tumor imaging techniques to facilitate accurate positioning of a tissue cauterization device.

It would also be desirable to provide methods and apparatus for treating tumors wherein an energy applicator could be tailored to the size and shape of the tumor, as quantified, for example, using tumor imaging techniques.

It would be desirable to provide methods and apparatus for treating abnormal tissue that include an automatic shut-off control, with suitable visual and/or audible indicators, that signal when therapy is complete, i.e., when a predetermined volume of tissue has been cauterized.

It would further be desirable to provide methods and apparatus for treating abnormal tissue that includes an expandable geometry that provides increased treatment surface area while in-situ but a relatively smaller insertion diameter, thereby reducing insertion trauma.

It yet further would be desirable to provide methods and apparatus for performing therapeutic cauterization of tissue using commonly available electrosurgical generators.

SUMMARY OF THE INVENTION

In view of the foregoing, it is an object of this invention to provide methods and apparatus, for use with existing tumor imaging techniques, capable of applying therapeutic hyperthermia, in situ, to any tumor which may be identified using minimally invasive procedures.

It is another object of the present invention to provide methods and apparatus for effecting complete necrosis of an identified tumor mass of predetermined volume, with minimal damage to surrounding healthy tissue. In particular, it is intended that the methods and apparatus of the present invention preferably enable treatment of a tumor of predetermined volume within a brief period of time (e.g., several seconds to tens of seconds).

It is a further object of this invention to provide methods and apparatus for effecting the treatment of a tumor promptly after completion of a biopsy procedure, thus permitting utilization of the vectoring biopsy needle guide cannula and/or tumor imaging techniques to facilitate accurate positioning of a tissue cauterization device.

It is another object of the invention to provide methods and apparatus for treating tumors wherein an energy applicator may be tailored or selected based on the size and shape of the tumor, as quantified, for example, using tumor imaging techniques.

It is a still further object of the invention to provide methods and apparatus for treating abnormal tissue including automatic shut-off of the treatment, with suitable visual and/or audible indicators, when therapy is complete, i.e., when a predetermined volume of tissue has been cauterized.

It is another object to provide methods and apparatus for treating abnormal tissue that includes an expandable geometry that provides increased treatment surface area while in-situ but a relatively smaller insertion diameter, thus reducing insertion trauma.

It is yet another object of the present invention to provide methods and apparatus for performing therapeutic cauterization of tissue using commonly available electrosurgical generators. In particular, devices constructed in accordance with the present invention may be designed to be compatible with previously known electrosurgical generators by accepting the available voltages and impedances of such generators, thereby eliminating the need for specialty generators.

In accordance with the present invention, apparatus is provided comprising two or more electrodes which are electrically isolated from one another, so that the only path for the flow of electrical current is through tissue contacting the electrodes. In accordance with the principles of the present invention, the apparatus permits selection of the electrode size and spacing, so that a predetermined volume of tissue may be heated to a temperature sufficient to cause irreversible necrosis. The two or more electrodes are disposed on either a rigid or flexible cannula or catheter.

Apparatus constructed in accordance with the invention allows application of therapeutic heating to a target tissue site promptly after a tissue biopsy procedure. When the tissue treatment applicator is used in conjunction with existing electrosurgical generators, a battery-powered control device may be provided, which may also serve as a handle for the apparatus. The device could include controls for initiating therapy and control circuitry that interrupts application of power to an energy applicator after a preselected time duration and/or current reduction ratio has been attained.

Alternatively, a specially designed radio-frequency power supply may be used (instead of a previously known electrosurgical generator) that incorporates controls for initiating therapy and circuitry for interrupting the application of power to the energy applicator after a predetermined time duration or when a predetermined current reduction ratio has been attained.

The apparatus of the present invention further utilizes electrode geometry to predictably control the size and shape of the tissue mass cauterized. Accordingly, the clinician may adjust or select an energy applicator configuration appropriate for the predetermined size and shape of the tumor to be treated, so that tissue temperatures in the range of 70 degrees C. (sufficient to cause cell death), but preferably less than 100 degrees C., may be achieved within relatively brief periods, thus reducing risk of injury to adjacent healthy tissue.

A further alternative embodiment of the present invention includes one or more expandable electrodes that may be expanded, once inserted in the tissue mass to be cauterized, to provide an increased electrode surface area during the energy application step, while reducing the diameter of the energy applicator during insertion.

In accordance with the methods of the present invention, patient physical discomfort and mental stress are reduced by: (1) the use of a local anesthetic applied to the site of the intended cauterization and (2) the completion of the therapeutic cauterization of tissue soon after completion of the biopsy procedure. In addition, the costs associated with medical treatment are reduced since therapy can be completed within the same time frame previously required for a biopsy procedure alone.

BRIEF DESCRIPTION OF THE DRAWINGS

Further features and advantages of the invention will become more apparent from the accompanying drawings and the following detailed description of the preferred embodiments, in which.

DETAILED DESCRIPTION OF THE PREFERRED EMBODIMENTS

Figure 1:
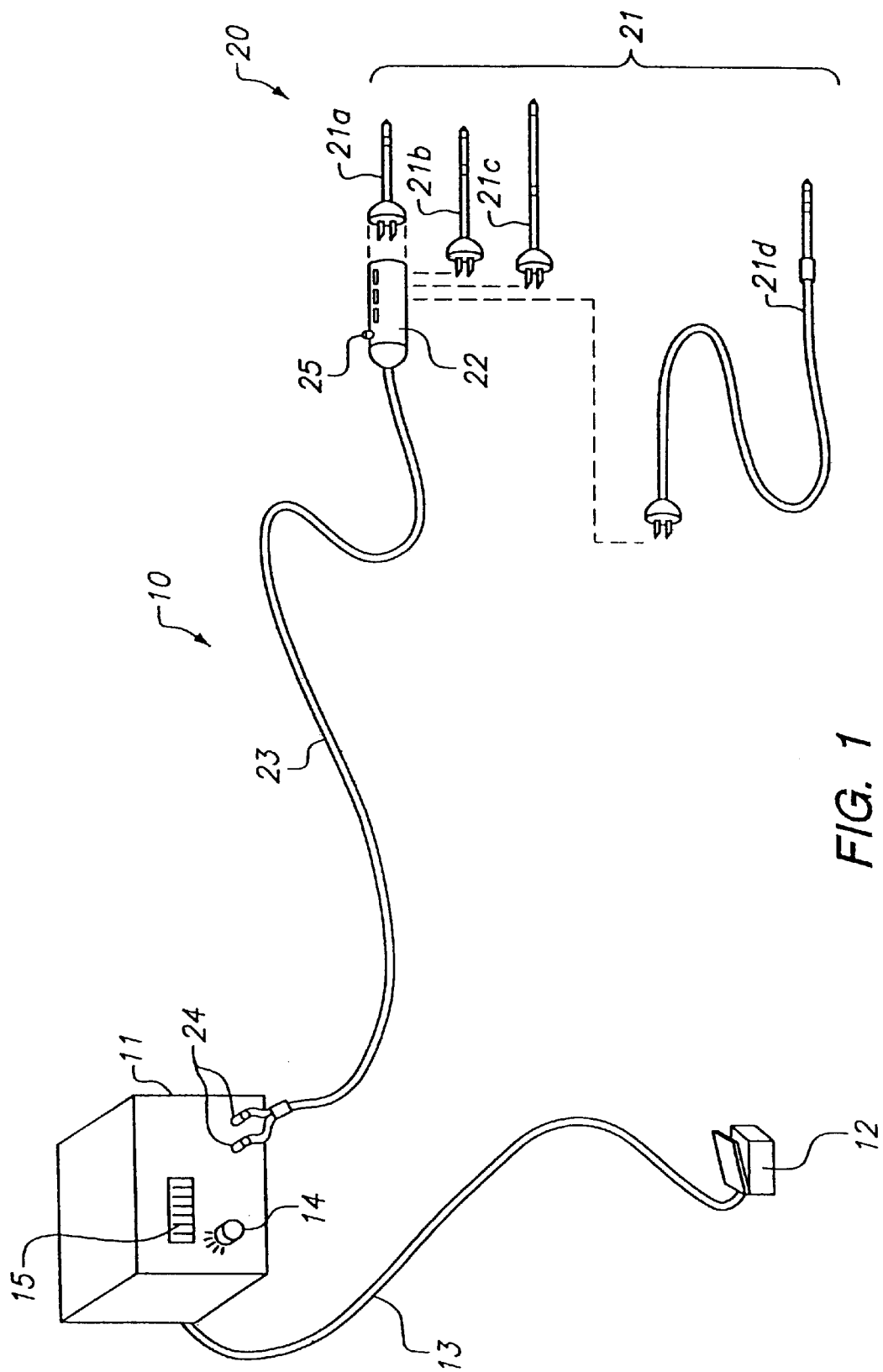
FIG. 1 is a perspective view of apparatus constructed in accordance with the present invention, including various energy applicators, together with a power source.

Referring to FIG. 1, apparatus 10 includes power source 11 and therapeutic cauterization device 20 comprising a plurality of energy applicators 21a–21d and control device 22 that accepts and activates a selected one of the energy applicators. Control device 22 is coupled to power source 11 by cable 23 using connectors 24. Energy applicator 21 is energized by activation of switch 25 on control device 22, in conjunction with foot pedal 12. Foot pedal 12 is coupled to power source 11 by cable 13.

Power source 11 may be any one of a wide range of previously known and commercially available electrosurgical generators, such as the Valleylab Force 2 electrosurgical generator, sold by Valleylab Inc., Boulder, Colo. Power source 11 includes at least power level (or voltage level) control 14 and power level (or voltage level) set point indicator 15, to allow a clinician to adjust the output of the power source to a set point level appropriate for the intended therapy. Alternatively, power source 11 may be a specially designed electrosurgical controller unit that incorporates the control and set point circuitry described in detail hereinafter with respect to FIGS. 2A and 2B.

In accordance with the present invention, energy applicators 21 come in a range of sizes and styles designed for effecting cauterization of predetermined volumes of tissue. Energy applicators 21a–21c illustratively comprise two or more electrodes disposed on a rigid or bendable needle or cannula, and operable in a bipolar mode for cauterizing specified volumes of tissue when activated for specified durations at predefined power levels.

Alternative embodiment of energy applicator 21d, also available with a range of electrode configurations (only one shown), also includes two or more electrodes disposed on a flexible catheter for percutaneous use. Other embodiments (not shown) may feature energy applicators employing flexible cannulas so that energy applicator 21 can be introduced to a treatment site through a tortuous body lumen or by using a previously known steerable catheter delivery system, thus permitting treatment of diseased tissue in the brain, prostate, uterus, bladder, lung, esophagus, liver, stomach and bowel. Preferably, energy applicators 21a–d all may be employed with common control device 22 using a plug-in arrangement described hereinafter.

Figure 2A:
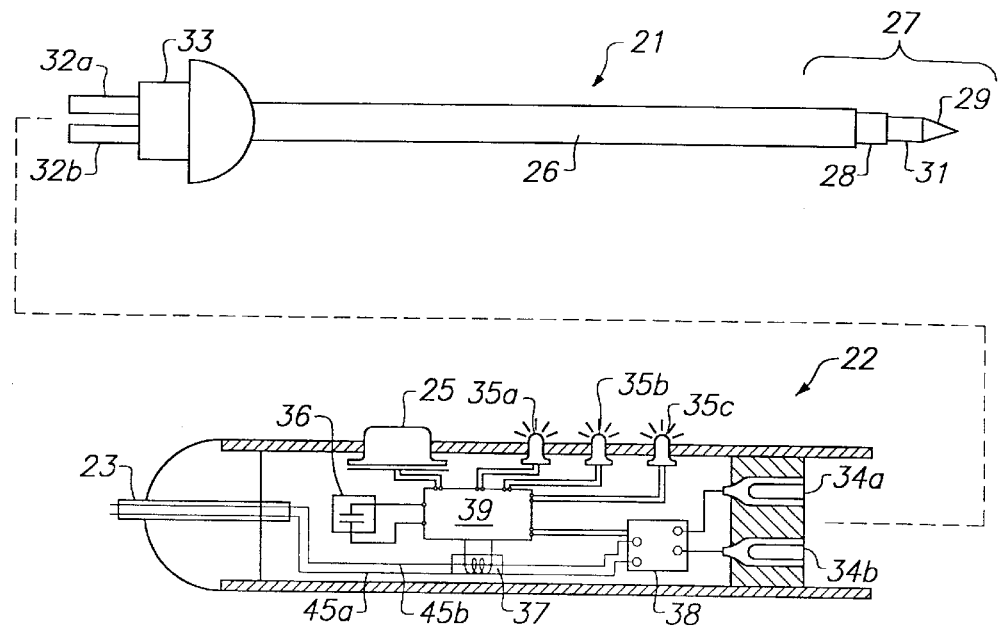
FIGS. 2A and 2B are side views of an illustrative energy applicator and associated control device constructed in accordance with the present invention.
Figure 2B:
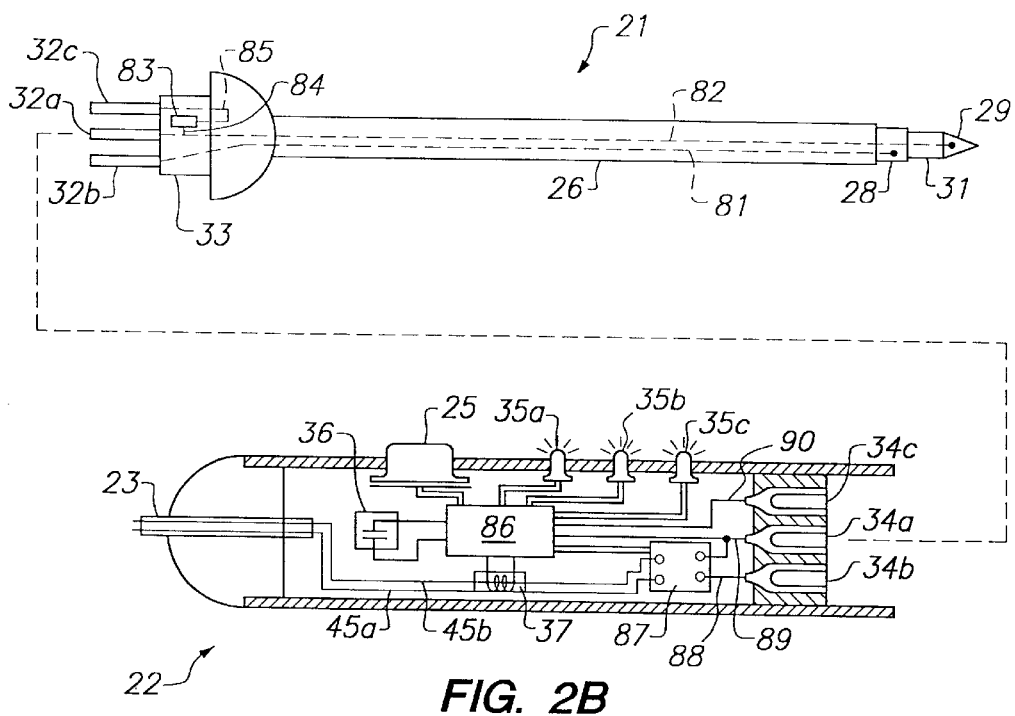
Figure 3:
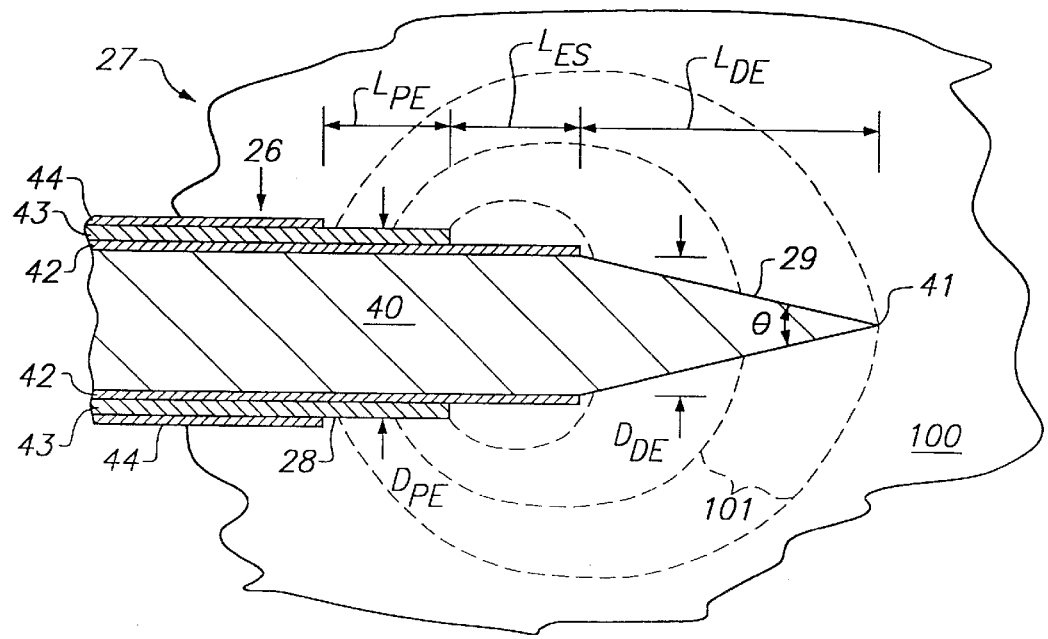
FIG. 3 is a partial sectional view of the distal tip of the energy applicator of FIGS. 2, showing an illustrative electric field resulting from activation of the energy applicator.

Referring now to FIGS. 2A, 2B and 3, illustrative energy applicators 21 constructed in accordance with the present invention is described. In FIG. 2A, energy applicator 21 comprises base cannula 26 having distal region 27 carrying two or more electrodes operable in a bipolar mode. The length of cannula 26 is dependent on the depth at which a target tissue site is located, typically, several to tens of centimeters from the external surface of a patient's body.

Proximal electrode 28 and distal electrode 29, which are electrically insulated from one another by insulated region 31, conduct radio-frequency current from power source 11 into tissue surrounding distal region 27 when activated. Energy applicator 21 connects to control device 22 (and is electrically coupled thereto) by insertion of plugs 32a and 32b extending from hub 33 into mating electrical receptacles 34a and 34b of control device 22.

With respect to FIG. 3, distal region 27 of energy applicator 21 is described in greater detail. Cannula 26 comprises shaft 40 comprising an electrically conducting material (e.g. metal or alloy) having sharpened distal tip 41. Distal tip 41 serves as distal electrode 29, and has a length of $L_{DE}$ and diameter $D_{DE}$. A thin layer of electrical insulation 42 is disposed on the external surface of shaft 40 up to (but not including) distal electrode 29. A layer of electrically conductive material 43 is disposed on the layer of electrical insulation 42 to form annular proximal electrode 28, having outer diameter $D_{PE}$.

A further layer of electrical insulation 44 is disposed on electrically conductive material 43 for the length of cannula 26 (except for the length $L_{PE}$ of electrically conductive material 43 exposed to form proximal electrode 28). The layer of electrical insulating material 42 provides electrical insulation between distal electrode 29 and proximal electrode 28, the length between the proximal edge of distal electrode 29 and the distal edge of proximal electrode 28 defining interelectrode spacing $L_{ES}$.

Electrically conductive material 43 is illustratively shown as comprising a metal or alloy annular tubing that extends from the proximal end of energy applicator 21. One of skill in the art of electrosurgical devices will appreciate that proximal electrode 28 and distal electrode 29 may also comprise metal-filled films disposed only for the length of the respective electrodes. In this latter case, suitable conductive traces or wires must be provided to connect the electrodes to plugs 32a or 32b.

Distal tip 41 of shaft 40 has a sharpened end forming an angle preferably in a range of about 20 to 40 degrees to facilitate insertion of energy applicator 21 into the tissue to be treated. Shaft 40 therefore preferably comprises a material capable of retaining a sharp tip, for example, Type 304 stainless steel.

Energy applicator 21 preferably comprises biocompatible materials and preferably has an overall size of between about 2 to 20 French (i.e., diameter of about 1.4 to 6.7 mm). Electrically insulating materials 42 and 44 preferably have thicknesses of about 0.002 inches (0.05 mm) and are selected to minimize the overall diameter of energy applicator 21. In FIG. 3, proximal electrode 28 illustratively comprises a thin-walled metal tube, such as stainless steel hypodermic tubing, having a wall thickness of 0.002 inch to 0.010 inch, and preferably 0.005 inch (0.13 mm) and a gauge size of about 2 to 20 French depending on the size of the tumor being treated. Electrically insulating materials 42 and 44 may comprise shrink tubing or be formed of a deposited insulating coating, such as Parylene, available from Specialty Coating Systems, Inc. Indianapolis, Ind.

An illustrative energy applicator designed in accordance with the principles of the present invention may be characterized by the following set of dimensional parameters: $L_{DE}$=6.2 mm and $D_{DE}$=3.3 mm, $L_{ES}$=1.9 mm, $L_{PE}$=3.3 mm and $D_{PE}$=3.7 mm, and an overall outside diameter of 3.8 mm.

Still referring to FIG. 2A, control device 22, which preferably serves as a reusable handle of the therapeutic cauterization device, is coupled to power supply 11 via cable 23. Control device 22 includes switch 25, lights 35a–35c, battery 36, current sensor 37 and limit circuit 38 coupled to control circuit 39. Wires 45a and 45b couple receptacles 34a and 34b to cable 23 via limit circuit 38, which may comprise, for example, a double pole switch. Switch 25, when depressed, causes lights 35a–35c to be individually illuminated, thereby indicating the status of the device, as described hereinbelow. A presterilized energy applicator is coupled to control device 22 by urging plugs 32a and 32b of the energy applicator into receptacles 34a and 34b of the control device.

Operation of the therapeutic cauterization device of FIG. 2A is now described. First, a clinician selects a presterilized energy applicator 21 appropriate for the size and shape of the tumor to be treated, and connects it to control device 22. Power supply 11 is then turned on and adjusted to provide an appropriate output signal for that energy applicator.

The clinician first depresses switch 25 to check the status of the apparatus. If the voltage level of battery 36 is at an acceptable level and all other circuitry is in a "ready" state according to preprogrammed logic contained within control circuit 39, green light 35a flashes, indicating that therapeutic cauterization may be initiated by depressing footpedal 12. If the preprogrammed logic of control circuit 39 indicates that the device is in a "not ready" state (e.g., due to low battery), orange light 35b flashes, indicating that correction of the fault condition is required.

If the green light flashes during the system check, the clinician may next administer a local anesthetic to the patient and insert distal region 27 of energy applicator 21 into the patient's tissue, for example, guided by ultrasound or radiographic images. For example, the imaging system described in commonly assigned U.S. patent application Ser. No. 08/421,381, now U.S. Pat. No. 5,660,185, may be used to position distal region 27 of energy applicator 21 within the tissue at target site.

Once the distal region of the energy applicator is properly positioned, the clinician depresses footpedal 12 (or another switch controlling activation of power source 11) to initiate application of radio-frequency voltage between proximal and distal electrodes 28 and 29, thereby causing current to flow through the tissue which effects the joulean heating of, and thereby, thermal necrosis of the tissue within a volume defined by electrode parameters $L_{DE}$, $D_{DE}$, $L_{PE}$, $D_{PE}$ and $L_{ES}$ of the energy applicator.

In accordance with the principles of the present invention, the preprogrammed logic within control circuit 39 monitors the current flow in wire 45b using current sensor 37, which communicates a sensed voltage to control circuit 39. When the current level sensed by current sensor 37 decreases from its initial value (e.g., obtained within a sample and hold period of about 100 msec following initial activation of the energy applicator) to a predetermined level (e.g., about one-fifth to one-tenth the initial current level), control circuit 39 causes double-pole switch 38 to be opened, thereby interrupting further application of current from power source 11. Simultaneously with causing the opening of limit circuit 38, control circuit 39 causes red light 35c to begin flashing, thus providing an indication to the clinician that treatment is complete. Control device 22 in addition may activate an audible indicator when red light 35c is illuminated.

Alternatively, control circuit 39 may include timer logic that is used in addition to or instead of current sensor 37 to terminate application of power after a predetermined period (e.g., 5 to 10 seconds). If both current and time of activation are monitored, control circuit 39 preferably is programmed to open limit circuit 38 (e.g., a double pole switch) and activate light 35c as soon as either limit is reached (i.e., current reduction or time duration). Preferably, no further activation of energy applicator 21 can occur until switch 25 is again depressed, thereby resetting the program logic of control circuit 39.

During cauterization, the power delivered to the electrodes is controlled so that the power density (watts/cm$^2$) at the electrode/tissue interface or the current density (amps/cm$^2$) through the intervening tissue between electrodes does not exceed a predetermined limit. Below this limit, boiling of cellular liquids leading to the generation of steam, and rapid increase in tissue impedance due to desiccation, may be minimized. It has been found that rapid desiccation of tissue can be minimized during purposeful cauterization of tissue by maintaining the power density at the electrode/tissue interface below about 250 watts/cm$^2$ or the current density to below about 5 amps/cm$^2$.

The exposed areas of the electrodes of energy applicator 21 preferably are designed to be of similar area, for example, differing by less than 25%. However, as described hereinabove, the exposed electrode areas for any particular energy applicator may vary over a wide range, depending on the size of the target tissue volume to be cauterized and the characteristics of the target tissue. Accordingly, each energy applicator 21 may be supplied with a recommended set of power or voltage settings with which that energy applicator may be used with selected commercially available power sources.

Alternatively, power control circuitry that maintains the time-averaged power and/or current application below a limit value corresponding to the selected electrode parameters can be incorporated into control device 22. If both time-averaged power and current are being controlled, then a limit value may be applied for each of the time-averaged power and current application. In the illustrative embodiment of FIG. 2B, a predetermined limit value may be set within the power control device 22 based on "coding" or identifying circuit element 83 (e.g., a resistor or capacitor) contained within energy applicator 21. In FIG. 2B, in which elements of the embodiment of FIG. 2A are indicated by like reference numerals, "coding" or identifying circuit element 83 is connected to plugs 32a and 32c via leads 84 and 85, respectively.

Still referring to FIG. 2B, energy applicator 21 is coupled to control device 22 by inserting plugs 32a, 32b and 32c into receptacles 34a, 34b and 34c, respectively. Upon initial insertion, control circuit 86 measures a value of a parameter of circuit element 83 (e.g., resistance or capacitance) and sets an upper power and/or current limit value which is used during the period of power application to control maximum power and/or current delivery and, accordingly, maximum power density and/or current density applied to tissue. When the applied power and/or current level reaches the set limit, control circuit 86 interrupts current flow for brief periods using, for example, limit circuit 87, so that the average power and/or current level (for example, the current level integrated over 100 milliseconds) remains below the limit value.

Alternatively, the energy applicator of FIG. 2B may be constructed with circuit element 83 disposed between lead wires 81 and 82 so that control circuit 86 measures a value of a parameter of circuit element 83 when electrodes 28 and 29 are open-circuited (i.e., not in contact with the tissue). In such an embodiment, plug 32c would be unnecessary, and could be omitted.

Other power and/or current control limit elements 87 can also be employed using designs well known to those skilled in the art. For example, circuit element 83 may form part of a bridge circuit or other suitable analog circuit, known to those skilled in the art, which limits the maximum amount of power or current that can be applied according to the size and surface area of the electrodes of energy applicator 21.

As illustrated in FIG. 3, when a voltage difference is applied between proximal electrode 28 and distal electrode 29 (and while distal region 27 is disposed within biological tissue 100), current flows between the electrodes along current flux lines 101 to effect Joulean heating in the tissue in accordance with Ohm's law (i.e., as the product of (current)$^2$×(tissue impedance)).

As the load impedance of the tissue decreases below 100 ohms, the output voltage and power output of conventional power sources (such as the Valleylab Force 2) decrease monotonically to zero, until no power is output when there is no load impedance. Also, as the load impedance increases from 100 to 1000 ohms, the output power again decreases monotonically, approaching a ten-fold lower output level at a 1000 ohm load impedance. At this ten-fold lower level, the power output is insufficient to raise the tissue temperature in the cauterization zone around the electrodes to a level that will result in irreversible necrosis of the tissue.

The impedance of most biological tissue increases when it is cauterized because of a change in the distribution of electrically conducting cellular fluids and an increase in the cellular membrane/fluid interface impedance. Accordingly, once a sufficient volume of tissue located between the electrodes of the energy applicator becomes cauterized, the current flow is restricted and current sensor 37 will detect a decrease in current level. When this decrease in current level (as sensed by current sensor 37) is detected by control circuit 39 (or control circuit 86 of the embodiment of FIG. 2B), the control circuit in turn interrupts supply of power to the energy applicator.

In accordance with the present invention, electrode parameters $L_{DE}$, $D_{DE}$, $L_{PE}$, $D_{PE}$ and $L_{ES}$ may be selected to effect the therapeutic cauterization of a predetermined volume 111 when placed in biological tissue 100. The capability to predict the cauterized volume based on electrode parameters $L_{DE}$, $D_{DE}$, $D_{PE}$ and $L_{ES}$ enables power to be applied for a preset period of time sufficient to effect the cauterization of the entire volume of tissue. The duration of power application required depends on the electrode parameters and the electrical characteristics of the biological tissue. For example, fatty tissue has relatively higher electrical impedance than lean tissue, and requires a longer period of power application than more vascularized tissue (e.g., fascia).

Figure 4:
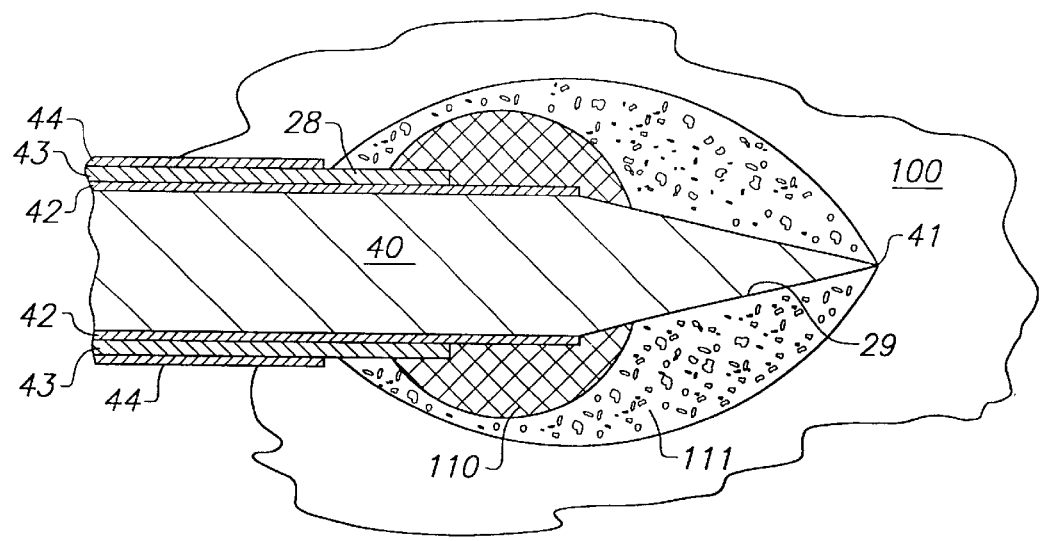
FIG. 4 is a partial sectional view of the distal tip of the energy applicator of FIGS. 2, showing a predetermined volume of cauterized tissue resulting from activation of the energy applicator.

Referring now to FIG. 4, spherical region 110 (represented by cross-hatching) is completely cauterized within about 2 seconds after the application of 50 watts of power through electrodes 28 and 29. Cauterization then progresses throughout cauterization zone 111 with continued application of power, until the self-limiting stage is attained in about 5–7 seconds.

Figure 5A:
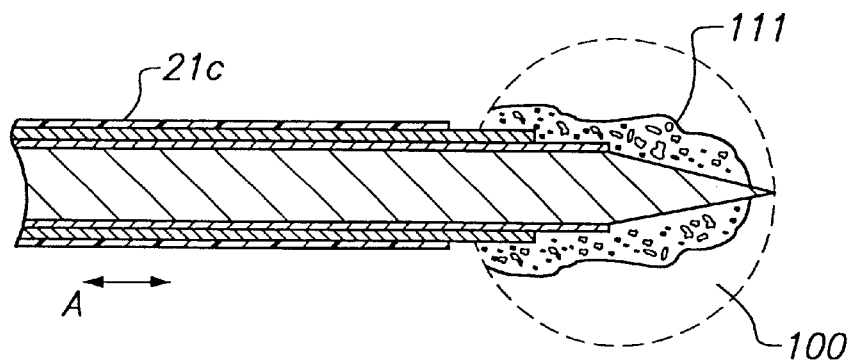
FIGS. 5A–5C are views showing the effect on the volume of tissue treated for different values of electrode parameters and also illustrating use of telescoping components in accordance with one family of embodiments of the present invention.
Figure 5B:
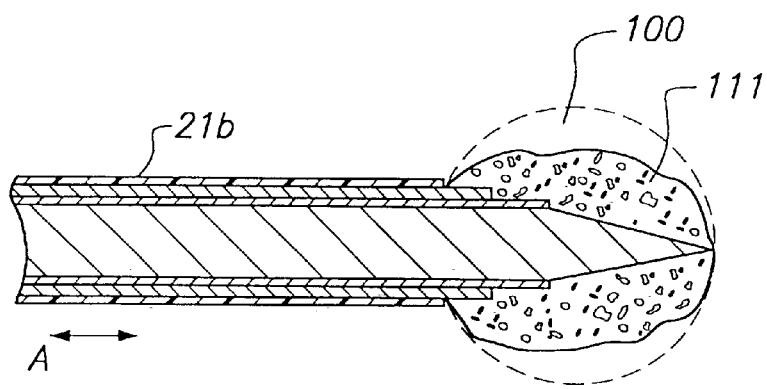
Figure 5C:
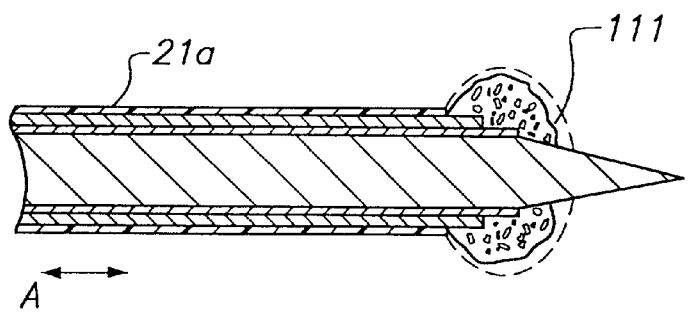

As depicted in FIGS. 5A to 5C, applicant has observed that as interelectrode spacing $L_{ES}$ increases, cauterization zone 111 becomes more elliptical. As the interelectrode spacing continues to increase, the cauterization zone develops into two lobes (with one lobe centered on each electrode) and a mid-region of incomplete cauterization between the two lobes. This is because current density is too low in the mid-region to provide effective cauterization of the tissue.

As shown in FIGS. 5B and 5C, cauterization zone 111 tends to become more spherical as interelectrode spacing $L_{ES}$ decreases. As the interelectrode spacing decreases and the cauterization zone becomes more spherical, electrode parameters $L_{PE}$, $L_{DE}$, $D_{PE}$ and $D_{DE}$ increasingly dictate the size of the cauterization zone relative to the effect of interelectrode spacing.

In accordance with the principles of the invention, in one embodiment of the therapeutic cauterization device, a plurality of energy applicators 21a–21d are provided, each having different electrode parameters $L_{PE}$, $L_{DE}$, $D_{PE}$, $D_{DE}$ and $L_{ES}$ that are established at the time of manufacture to effect the complete cauterization of different predetermined volumes 111.

For example, in FIGS. 5A–5C, each distal region 27 of the respective energy applicators 21a–21c is constructed to treat a specified predetermined volume 111. Accordingly, the clinician may select an energy applicator to treat a tumor having a size and shape that has been determined by the clinician using suitable tumor imaging techniques (e.g., using radiography and/or ultrasonography methods).

In an alternative embodiment of the apparatus of the present invention, the energy applicator may be designed so that electrode parameters $L_{PE}$, $L_{DE}$, and $L_{ES}$ may be adjusted by the clinician at the time of treatment.

In this embodiment, each of insulating layers 42 and 44 and electrically conducting material 43 may be designed to telescope with respect to one another (indicated by directional arrows A in FIGS. 5A–5C), thereby allowing the components of the energy applicator to be slidingly displaced with respect to one another to individually vary the lengths of the proximal and distal electrodes and interelectrode spacing.

In accordance with this alternative embodiment, a single energy applicator could be configured to provide any of the energy applicators 21a–21c depicted in FIGS. 5A–5C. It is contemplated that a clinician using such an embodiment of the invention would, after determining the size and shape of a tumor, consult a table specifying the electrode parameters to which the energy applicator should be adjusted, together with the appropriate power settings for power source 11. Separate energy applicators may be supplied having varying diameters to affect larger or smaller cauterization zones.

Studies conducted on flank steak, turkey breast and poultry egg albumen as surrogate tissue media permit the cauterization zone volume to be quantitatively related to the electrode parameters of the energy applicator. During these studies, the energy applicator was applied to the surrogate tissue media to cauterize a portion of the tissue. The tissue was then analyzed under a video microscope using a scalpel blade to identify the cauterization zone.

Such studies have revealed that, within one to two seconds after power application, only fractional volume 110 (see FIG. 4) of tissue is cauterized, located between the proximal edge of the distal electrode 29 and the distal edge of proximal electrode 28. If therapy were terminated at this point in time, volume 111 would not be completely cauterized, thus leaving some diseased or abnormal biological tissue untreated. By contrast, if a temperature sensor were positioned within volume 110, as suggested by some previously known devices, the temperature measurement would incorrectly indicate that the target tissue had reached the preselected temperature level when, in fact, only a fraction of the total desired treatment volume had reached a temperature sufficient for necrosis.

Figure 6:
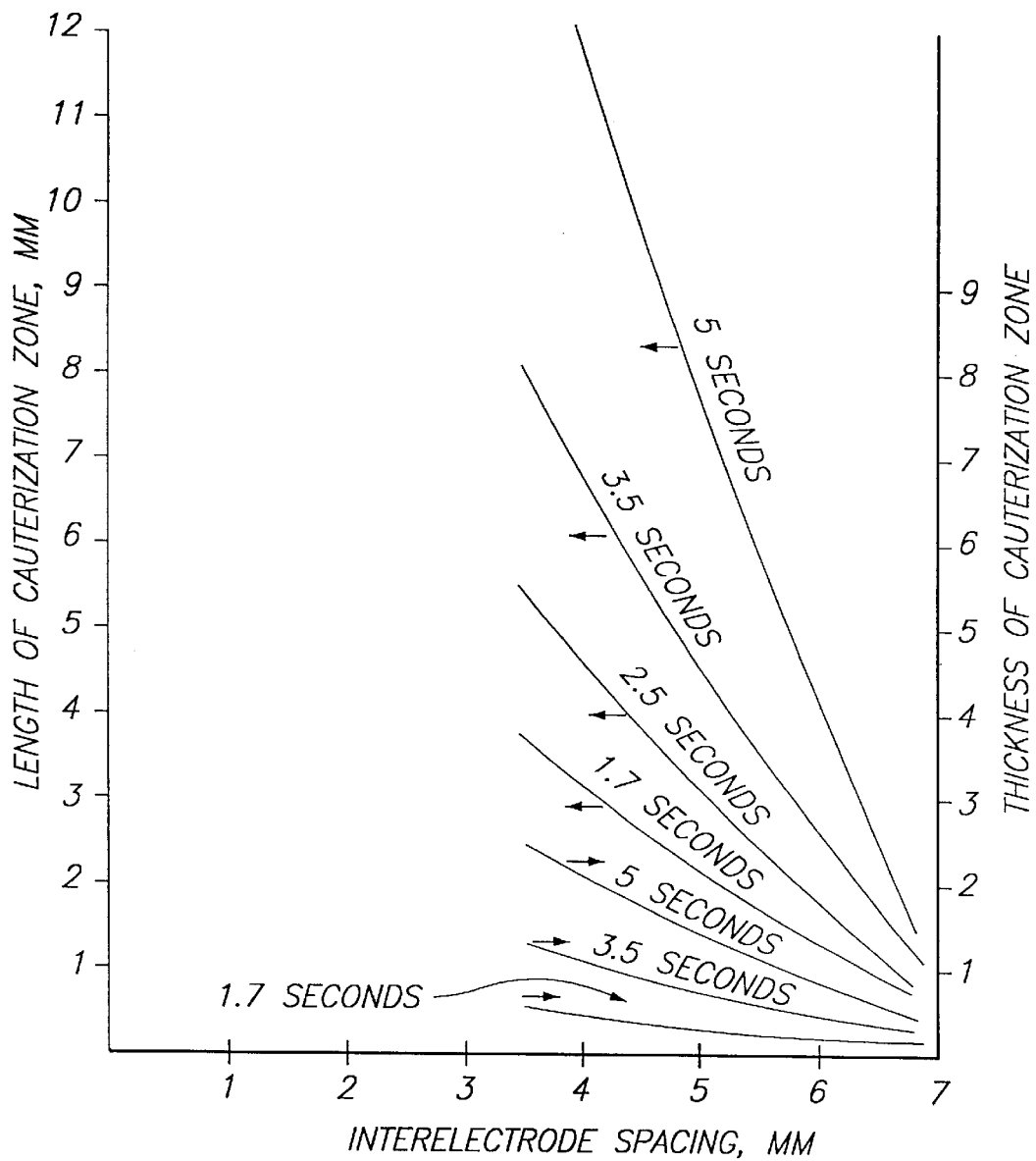
FIG. 6 is a graph illustrating the effect that varying electrode parameters has on the predetermined volume of the cauterization zone.

The foregoing studies have also demonstrated how the shape of the cauterization zone changes as a function of the electrode parameters and time, as shown in FIG. 6. In particular, the cauterization zone thickness and length are affected by the interelectrode spacing and the duration of time that energy is applied to the site. As will be apparent from FIG. 6, the length of the cauterization zone is effected more by the interelectrode spacing and the time duration than is the thickness of the cauterization zone. The length of the cauterization zone, as discussed above, is more sensitive to the interelectrode spacing, so that as the interelectrode spacing increases, up to the point at which two lobes develop, the cauterization zone becomes a more elongated ellipsoid.

It is contemplated that, given the foregoing results and the impedance measuring techniques described, for example, in U.S. patent application Ser. No. 08/398,644, now U.S. Pat. No. 5,630,426, a table of predetermined volumes producible using specified electrode parameters, power ranges, and durations may be compiled for different tissue types. It is further expected that in commercial embodiments of the therapeutic device of the present invention, energy applicators will be offered with a variety of electrode configurations to meet almost any clinical need.

Studies conducted on translucent poultry egg albumen enabled the time-dependent evolution of the cauterization zone during the application of radio-frequency current to be measured. These studies indicated that power should be supplied until there is a significant reduction in current flowing between the electrodes, as measured by current sensor 37 of control device 22. A reduction in current in the range of three-fold to twenty-fold, and more particularly, five-old to ten-fold, was found to produce complete cauterization.

Figure 7:
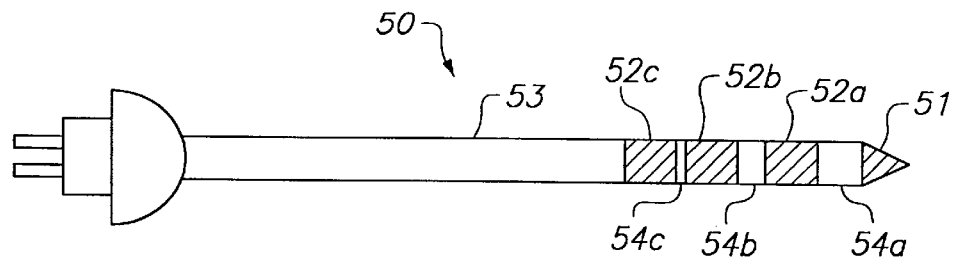
FIG. 7 is a side view of an alternative energy applicator constructed in accordance with the present invention.

Referring now to FIG. 7, an alternative embodiment of the present invention is described with respect to energy applicator 50. Energy applicator 50 includes distal electrode 51 and multiple proximal electrodes 52a, 52b and 52c disposed on cannula 53 with interposed insulating regions 54a, 54b and 54c. Electrodes 52a–52c may of the thin film type, so that a selected one of proximal electrodes 52a–52c may be energized in conjunction with distal electrode 51. The lengths of proximal electrodes 52a–52c, as well as the lengths of insulating regions 54a–54c, may vary along the length of cannula 53, so that for each one of proximal electrodes 52a–52c energized in combination with distal electrode 51 for a specified time, a corresponding predetermined volume of tissue is cauterized.

For instance, after determining the size and shape of a region of abnormal tissue, a clinician could consult a table similar to FIG. 6 that provides length and thickness of the cauterized zone as a function of the proximal electrode. The clinician then activates a desired proximal electrode, using a selector switch on the control device (not shown), to cauterize the region of abnormal tissue. Alternatively, or in addition, more than one of proximal electrodes 52a–52c may be energized in combination with distal electrode 51.

Figure 8A:
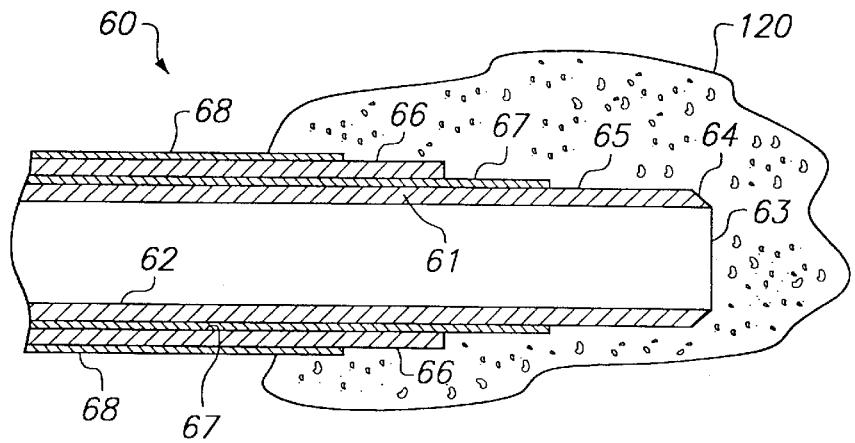
FIGS. 8A and 8B are partial cross-sectional views of an alternative embodiment of the energy applicator of the present invention suitable for use in performing a biopsy procedure.
Figure 8B:
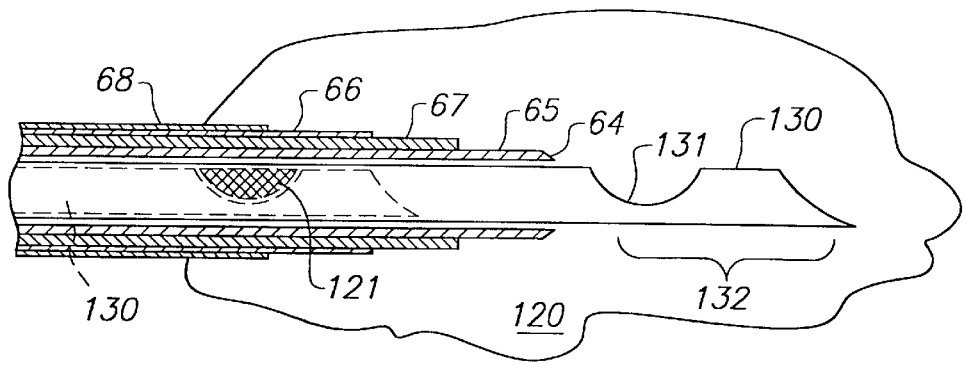

Referring now to FIGS. 8A and 8B, a yet further alternative embodiment is described in which energy applicator 60 includes tubular shaft 61 having lumen 62. Distal edge 63 of tubular shaft 61 preferably includes bevel 64 to facilitate introduction and advancement of the energy applicator into biological tissue 120, and includes an exposed region forming distal electrode 65. Energy applicator is otherwise similar in construction to energy applicators 21 of FIGS. 2, and includes proximal electrode 66 and insulation layers 67 and 68. The hub and control device used with energy applicator 60 are modified to allow the introduction and positioning of extraction device 70 (e.g., a biopsy needle) through lumen 62, as shown in FIG. 8B, for example, to permit aspiration of debris from the treatment site through lumen 62.

Referring to FIG. 8B, biopsy needle 130 may be inserted through lumen 62 so that a portion of the tissue protrudes into cavity 131 formed in region 132 of the biopsy needle. When energy applicator 70 is then displaced distally along biopsy needle 130, bevel 64 of shaft 61 severs the tissue, thereby permitting sample of tissue 121 to be withdrawn for pathological examination prior to the initiation of therapeutic cauterization. The control device used with the energy applicator and biopsy needle of FIGS. 8 may advantageously include a mechanical, electromagnetic, or pneumatic advancement mechanism for actuating movement of shaft 61 to sever tissue sample 121. Accordingly, the embodiment of FIGS. 8 incorporates the electrode arrangement of the present invention as an integral part of a tissue biopsy device, so that a single device permits both tissue biopsy and therapeutic treatment.

Figure 9A:
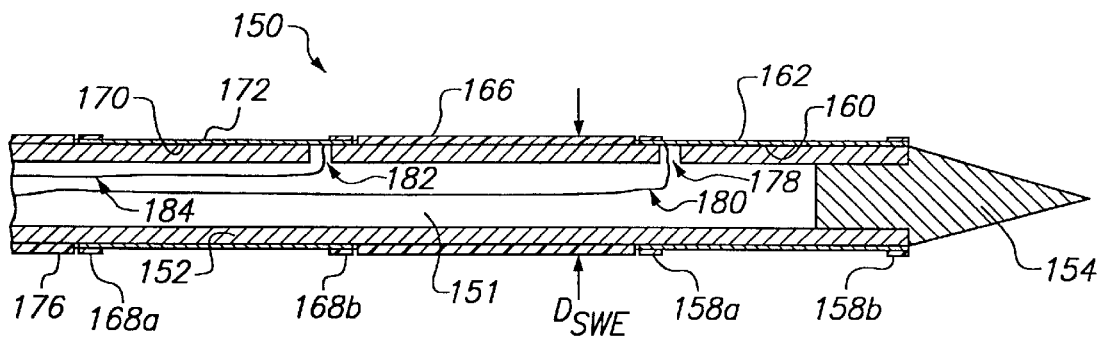
FIGS. 9A and 9B are, respectively, sectional and side views of the working end of a further alternative embodiment of the energy applicator of the present invention.
Figure 9B:
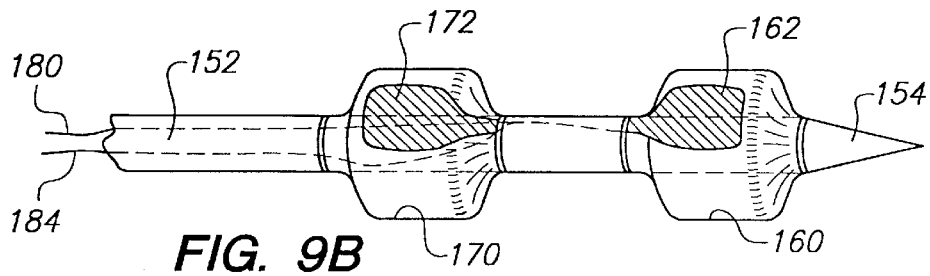

Referring now to FIGS. 9A and 9B, yet another embodiment of the energy applicator of the present invention is described. In this embodiment, working end 150 of energy applicator 21 comprises shaft 152 having trocar tip member 154. Trocar tip member 154 may be joined to shaft 152 using known methods, e.g., welding, brazing or adhesive bonding, as appropriate to the materials of construction. By way of example, shaft 152 and trocar tip member 154 may be manufactured using biocompatible metals such as stainless steel, titanium or nickel-based alloys. Expandable members 160 and 170 are located at the distal and proximal ends, respectively, of working end 150, and may be formed from an elastomeric material such as polyurethane or polyethylene teraphthalate.

A portion or all of the outer surfaces of distal and proximal expandable members 160 and 170 are covered with electrically conducting layers, such as films of stainless steel, silver, gold or other biocompatible metal or alloy, that form electrodes 162 and 172, respectively. In FIG. 9B, electrodes 162 and 172 illustratively cover only a portion of the circumference of expandable members 160 and 170.

Locking collars 158a and 158b are positioned at the proximal and distal ends, respectively, of expandable member 160 to provide a fluid tight seal between expandable member 160 and shaft 152. Likewise, locking collars 168a and 168b are positioned at the proximal and distal ends, respectively, of expandable member 170 to provide a fluid tight seal between expandable member 170 and shaft 152. Distal hole 178 and proximal hole 182 allow fluid communication between lumen 151 of shaft 152 and the annular spaces formed between shaft 152 and expandable members 160 and 170.

Electrically insulated lead wires 180 and 184 are brought into electrical communication with the electrodes 162 and 172, respectively, and terminate at the proximal end of the energy applicator at plugs 32a and 32b (see FIG. 2A). Electrically insulated lead wires 180 and 184 illustratively extend through holes 178 and 182, respectively and, in turn, are electrically attached to electrodes 162 and 172 using locking collars 158a and 168a, respectively.

The portion of shaft 152 between distal electrode 162 and proximal electrode 172 is covered with electrically insulating layer 166. Also, the portion of shaft 152 proximal of proximal electrode 172 is also covered with electrically insulating layer 176. Electrically insulating layers 166 and 176 may be formed using plastic sleeving (e.g., polyimide), heat shrink tubing (e.g., Kynar, polyester or polyolefin tubing) or may be formed of a deposited insulating coating such as Parylene.

The overall diameter, $D_{SWE}$, of working end 150, prior to inflation of expandable members 160 and 170, is expected typically to be in a range of 0.7 mm to 6.7 mm. When the energy applicator is positioned in tissue 100, so that working end 150 is brought into close proximity with a target tissue (e.g., tumor) or positioned such that the target tissue is located between proximal electrode 172 and distal electrode 162, expandable members 160 and 170 are inflated, as shown in FIGS. 9B and 10.

Figure 10:
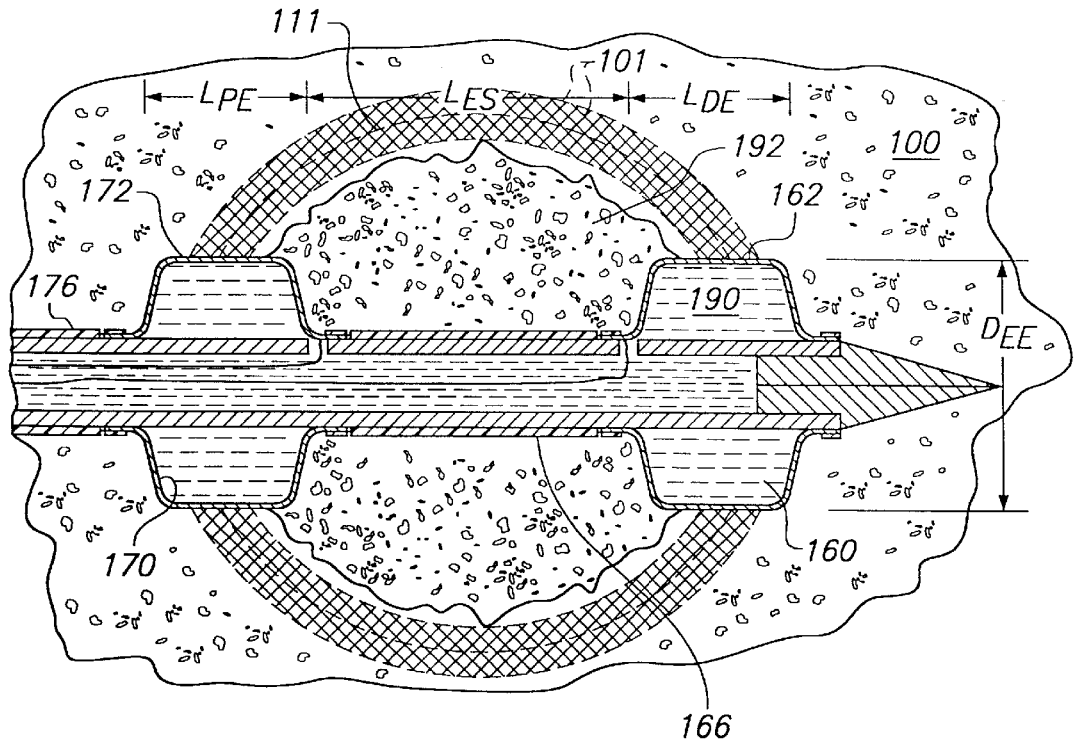
FIG. 10 is a sectional view of the distal tip of the energy applicator of FIGS. 9, showing an illustrative electric field and cauterization zone resulting from activation of the energy applicator.

Referring now to FIG. 10, working end 150 of the energy applicator of FIGS. 9 is shown positioned so that target tissue 192 (e.g., tumor) is located between distal electrode 162 and proximal electrode 172, with expandable members 160 and 170 being inflated. Working end 150 is first positioned in tissue 100 with distal electrode 162 and proximal electrode 172 in the unexpanded (i.e., minimum diameter) configuration, so as to minimize trauma to healthy tissue during the insertion step.

Once the proximal and distal electrodes are positioned relative to target tissue 192, as confirmed, for example, by fluoroscopy, radiography, ultrasonography or vectoring of a device based on previous mapping of target tissue (e.g., using computer aided tomography, magnetic resonance imaging and/or ultrasonography), expandable members 160 and 170 are inflated using suitable pressurizing fluid 190, such as sterile water or isotonic saline, to achieve the enlarged electrode shapes depicted in FIG. 10.

Once electrodes 162 and 172 are positioned with respect to target tissue 192 and inflated to expanded diameter $D_{EE}$, a high frequency voltage may be applied between plugs 32a and 32b at the proximal and of the energy applicator using the control device described hereinabove. Upon the application of an appropriate high frequency voltage to leads 180 and 184, current flows through tissue 100 located between electrodes 162 and 172, illustrated by current flux lines 101.

According to the selected sizes and spacing of electrodes 162 and 172 and the applied voltage and duration of energy application, a predefined volume of tissue 111 is cauterized due to the attainment of a current density in volume 111 sufficient to cause heating to above about 60 to 70° C., resulting in irreversible necrosis of tissue throughout volume 111, including target tissue 192. For volume 111 depicted in FIG. 10, electrodes 162 and 172 cover the entire circumference of expandable members 160 and 170. The duration of energy application by the method and apparatus of the present invention is typically expected to be in a range from several seconds to tens of seconds, depending upon the volume of tissue to be cauterized.

The dimensions of the expanded electrodes at working end 150 depend on the size and shape of the target tissue that requires cauterization. Typically, the diameter of the expanded electrodes, $D_{EE}$, ranges from 1 mm to 20 mm, the lengths of the proximal and distal electrodes, $L_{PE}$ and $L_{DE}$, and the interelectrode spacing, $L_{ES}$, range from 2 mm to 50 mm. The thickness of electrically insulating layers 166 and 176 range from 0.02 to 0.2 mm. The frequency of the applied voltage is preferably in a range of from 20 kHz to 40 MHZ, and more preferably in the range from 200 kHz to 2 MHZ. The applied voltage may be in a range of from 5 volts (RMS) to 1000 volts (RMS), depending on the size and interelectrode spacing of the electrodes as well as the operating frequency and electrical properties of the tissue being treated. The crest factor for the applied voltage is preferably in a range from 1 to 10, and more preferably, in the range from 1 to 2.

Figure 11:
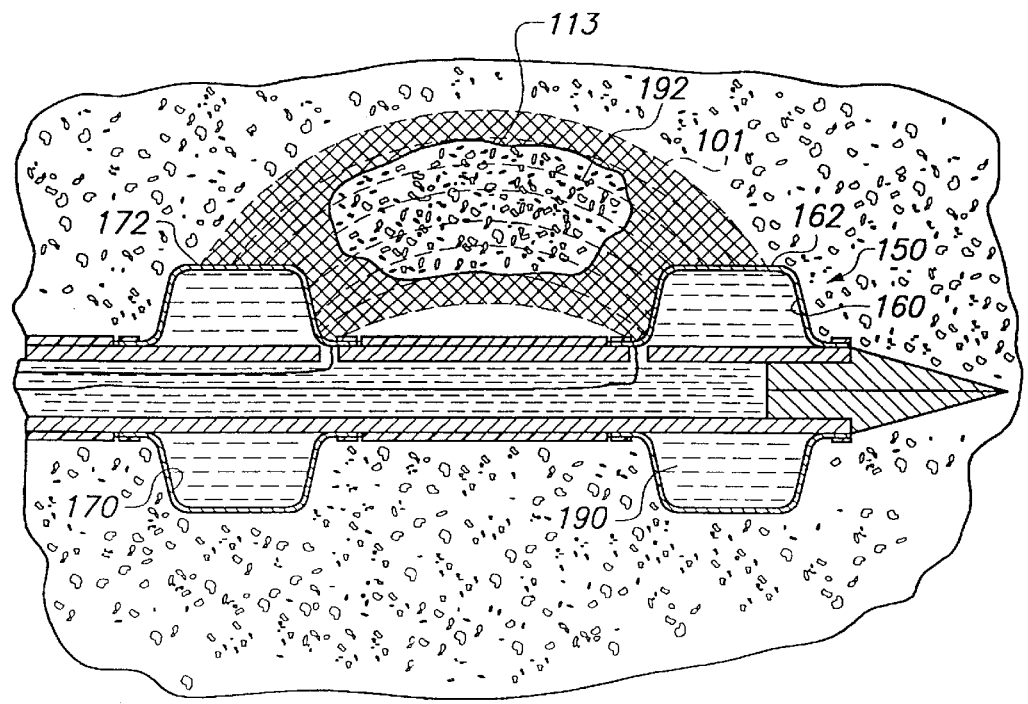
FIG. 11 is a view similar to that of FIG. 10 for an energy applicator having electrodes disposed over only a portion of the expandable members.

Referring now to FIGS. 9B and 11, an embodiment of working end 150 is described in which proximal electrode 172 and distal electrode 162 only cover a portion of expandable members 170 and 160, respectively. In all other regards, this embodiment is similar to that of FIGS. 9A and 10 described hereinabove. The embodiment of FIG. 9B is particularly useful in treating target tissue 192 (e.g., tumor) that is adjacent to the working end of the energy applicator, but not pierced by the working end as in FIG. 10. This arrangement may be preferred in some treatment situations to avoid iatrogenic metastases that might otherwise occur when the vascular network within malignant tissue is disrupted (e.g., if the trocar tip pierced the tumor).

In FIG. 11, working end 150 is positioned adjacent to target tissue 192, the proximal and distal electrodes are expanded, and voltage is applied between the electrodes, thereby causing current to flow in the localized region defined by current flux lines 101. According to the selected sizes and spacing of electrodes 162 and 172 and the applied voltage and duration of energy application, predefined volume of tissue 113 is cauterized due to the attainment of a current density in volume 113 sufficient to cause heating to above about 60° to 70° C., resulting in irreversible necrosis of tissue throughout volume 113 (including target tissue 192).

The use of electrodes that cover only a portion of the expandable members allows a predefined region of tissue to be cauterized that is adjacent to the working end of the energy applicator. Consequently, the volume of tissue cauterized is minimized, while also reducing the possibility of inducing iatrogenic metastases.

The embodiments of FIGS. 9 utilize one or more expandable electrodes that provide increased electrode surface area during the energy application step, while providing a reduced diameter of the energy application during the tissue insertion and positioning step. The increased electrode surface area provided by the expandable members enables the level of current and power that can be applied during the treatment step to be increased, relative to a constant diameter energy applicator, while preventing unwanted desiccation and steam generation due to boiling of tissue/cellular liquids. In addition, the increased electrode surface area also enables the duration of the energy application period to be reduced.

An additional benefit of the embodiment of FIGS. 9 is that electrical contact between the electrode surface and the adjacent tissue is enhanced because the expandable member (and electrode) are pressed against the surface of the adjacent tissue. The resulting reduction in interfacial contact impedance reduces localized heating at the electrode/tissue interface, and further reduces the potential for excessive localized heating and associated desiccation, which may otherwise lead to significant electrical impedance at the electrode/tissue interface.

Moreover, the preferred use of water or isotonic saline as the pressurizing fluid serves to moderate temperatures at the electrode/tissue interface, thereby further reducing localized tissue desiccation and/or water vapor generation at the electrode/tissue interface. Through the use of expandable electrodes, the diameter of the energy application may be maintained as small and atraumatic as possible, thereby allowing the use of the present invention in a wide range of applications, including office-based procedures, with little scarring and discomfort to the patient and reduced risk of iatrogenic injury to the patient.

Figure 12:
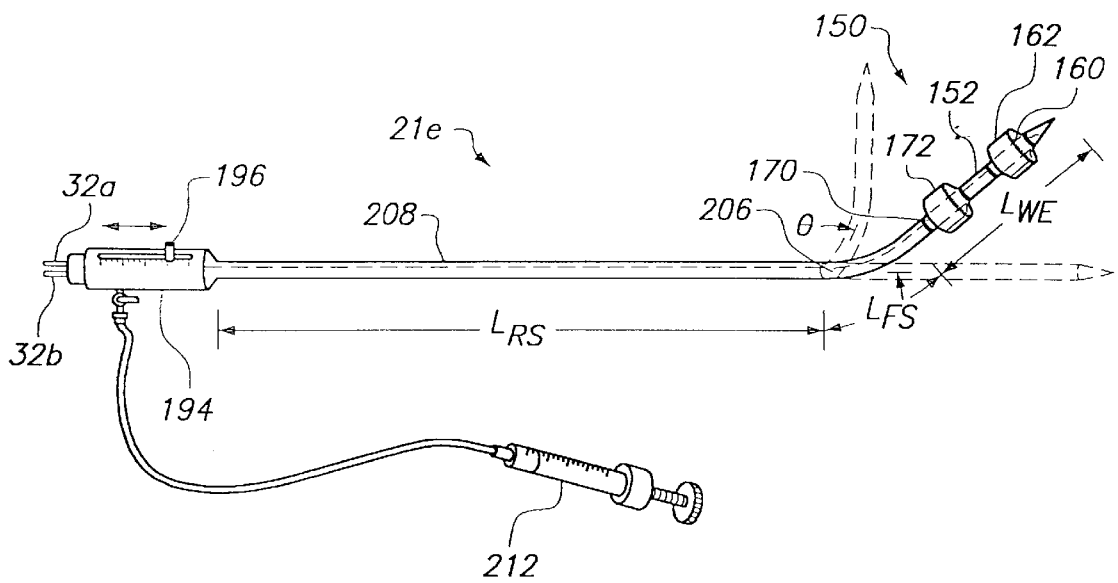
FIG. 12 is a perspective view of yet another alternative embodiment of an energy applicator constructed in accordance with the present invention.

With respect to FIG. 12, yet another embodiment of the energy applicator of the present invention is described. In this embodiment, the shaft of energy applicator 21e is divided into three distinct regions. The distal-most region comprises working end 150 as described hereinabove with respect to FIGS. 9, and may incorporate rigid shaft member 152 (e.g., stainless steel Type 304) and electrodes 162 and 172 disposed on expandable members 160 and 170, respectively. Flexible segment 206 is positioned between working end 150 and rigid support shaft 208. Support shaft 208 is, in turn, affixed to hub 194, which couples to control device 22. Hub 194 preferably includes mechanical actuation slider 196, which may be advanced or retracted to change the angular position of working end 150.

Alternatively, support shaft 208 may also be flexible, allowing its use within the channel provided in conventional flexible endoscopic devices. A pull wire between mechanical actuation slider 196 and the distal portion of the working end effects the controllable deflection of working end 150 relative to the axis of support shaft 208 through angle θ. The dimensions of the various segments depend on the size, shape and location of the target tissue within the body. Typically, working end length, $L_{WE}$ is expected to range from 6 mm to 100 mm, while the length of the support member $L_{RS}$, is expected to range from 5 cm to 200 cm. The length of flexible segment 206, $L_{FS}$, should be sufficiently long that angle θ of working end 150 may provide deflection through a range of from 0 to about 75°.

Syringe 212 or other pressurization device may be used to inject pressurizing fluid 190 into expandable members 160 and 170 to effect their controlled dilation, once working end 150 is properly positioned relative to the target tissue.

It should be understood that in all of the foregoing descriptions of the preferred embodiments, the target tissue is not limited to only tumors but also may include any tissue that a clinician may choose to treat, including, but not limited to, tissue in the prostate, uterus, esophagus, uvula, tonsils and adenoids.

It will be understood that the foregoing is merely illustrative of the apparatus and methods of the present invention, and that various modifications can be made by those skilled in the art without departing from the scope and spirit of the claimed invention.

What is claimed is:

1. Apparatus connectable with a power source to provide current flow based therapeutic cauterization of a volume of biological tissue, exhibiting a predetermined shape and size, the apparatus comprising:
    a base having a longitudinal axis;
    a distal electrode disposed on the base and having a surface area and configuration, energizable for effecting said therapeutic cauterization of said volume of biological tissue by deriving a current flow substantially only within a zone of current flow encompassing and conforming in correspondence with said tissue predetermined shape and size
    a proximal electrode disposed on the base and having a surface area and configuration energizable for effecting said therapeutic cauterization in operational association with said distal electrode, and being spaced and electrically isolated a length therefrom a distance corresponding with and establishing along said length said current flow with a shape of said zone encompassing and conforming in correspondence with said tissue shape and size; and
    control means for controllably, electrically coupling said distal electrode and said proximal electrode with said power source to effect said energization thereof.

2. The apparatus as defined in claim 1, wherein the proximal electrode is coaxial with the distal electrode.

3. The apparatus as defined in claim 2, wherein the distal electrode comprises a sharpened end of a solid cylindrical shaft.

4. The apparatus as defined in claim 2, wherein the distal electrode comprises a hollow cylindrical shaft.

5. The apparatus as defined in claim 4, wherein the distal electrode has a sharpened edge to facilitate introduction and advancement of the energy applicator into biological tissue.

6. The apparatus as defined in claim 4, wherein an extraction device is located within the hollow cylindrical shaft, the extraction device being operable in combination with the energy applicator to sever a sample of biological tissue.

7. The apparatus as defined in claim 1, wherein said control means comprises:
    control circuitry including a current detector that measures a current flowing between the proximal and distal electrodes during said energization, the current detector measuring a first current value upon initial energization of said distal and proximal electrodes and a second current value at an interval following said initial energization thereof; and wherein the control circuitry terminates activation of said electrodes when the present current value falls to a predetermined percentage of the initial current value.

8. The apparatus as defined in claim 7, wherein the control circuitry terminates energization of said electrodes when a present current value falls to a value between five and thirty percent of the initial current value.

9. The apparatus as defined in claim 1, wherein the proximal electrode is slidably adjustable along said axis with respect to the distal electrode.

10. The apparatus as defined in claim 1, comprising multiple said proximal electrodes that may be selectively energized in combination with the distal electrode.

11. The apparatus as defined in claim 1, wherein said control means further comprises:
a timer that measures a preset period of time from energization of said electrodes; and
circuitry that terminates supply of power to said electrodes when said preset period elapses.

12. The apparatus as defined in claim 1, wherein said control means further comprises:
a coding element; and
circuitry that measures a value of a parameter of the coding element to determine an upper power or current limit value corresponding to a maximum power density or current density to be applied to the biological tissue.

13. The apparatus as defined in claim 1, further comprising an expandable member having a contracted diameter for insertion into the biological tissue and an expanded diameter, one of the proximal electrode and distal electrode disposed on the expandable member.

14. The apparatus as defined in claim 13, further comprising means for injecting a pressurizing fluid into the expandable member, the pressurizing fluid moderating the temperature of the electrode disposed on the expandable member.

15. The apparatus of claim 1, in which:
said proximal electrode comprises an expandable member having a contracted diameter for insertion to a select position with respect to said biological tissue and actuable to an expanded diameter defining a proximal outer surface when operationally located with respect to said tissue predetermined volume; and
said proximal electrode surface area is disposed upon at least a portion of said proximal outer surface.

16. The apparatus of claim 15, in which:
said distal electrode comprises an expandable member having a contracted diameter for insertion to a select position with respect to said biological tissue and expandable to an expanded diameter defining a distal outer surface when operationally located with respect to said tissue; and
said distal electrode surface area is disposed upon at least a portion of said outer surface.

17. The apparatus of claim 1, in which:
said proximal electrode is disposed about said axis and said surface area thereof extends about said axis along a length, $L_{PE}$;
said distal electrode is disposed about said axis and extends therealong a length, $L_{DE}$;

said proximal electrode is spaced along said axis from said distal electrode a length, $L_{ES}$; and
said lengths $L_{PE}$, $L_{DE}$ and $L_{ES}$ are selected to effect said derivation of said zone of current flow encompassing said tissue predetermined shape and size.

18. The apparatus of claim 17, in which:
said distal electrode is configured having a maximum diameter, $D_{DE}$;
said proximal electrode is configured having a diameter, $D_{PE}$; and
said diameter $D_{DE}$ and $D_{PE}$ are selected to effect said derivation of said zone of current flow encompassing said tissue predetermined shape and size.

19. Apparatus connectible with a power source for providing current flow based therapeutic cauterization of a volume of biological tissue exhibiting a predetermined shape and size, the apparatus comprising:
an energy applicator having unique electrode parameters that provide cauterization of a predetermined volume of biological tissue when said energy applicator is activated, said applicator comprising:
a shaft having a longitudinal axis;
first and second mutually electrically isolated electrodes disposed on the shaft exhibiting respective surface areas and spaced apart a distance along the longitudinal axis, the distance between the first and second electrodes and said respective surface areas determining a current flow substantially only within a zone of size and shape encompassing and conforming with said volume predetermined shape and size of biological tissue; and
a handle that couples said applicator to the power source.

20. The apparatus as defined in claim 19, wherein the first and second electrodes are coaxially aligned.

21. The apparatus as defined in claim 19 wherein the shaft includes a lumen.

22. The apparatus as defined in claim 21, further comprising a biopsy cannula disposed within the lumen, the biopsy cannula operable to isolate by severance and remove a sample of biological tissue.

23. The apparatus as defined in claim 19 wherein the shaft has a sharpened tip to facilitate introduction and advancement of the energy applicator into biological tissue.

24. The apparatus as defined in claim 19, further comprising:
a current detector that measures a current level between the first and second electrodes, the current detector measuring an initial current value upon activation of the energy applicator and a present current value following initial activation of the energy applicator; and
circuitry for terminating the supply of power to the energy applicator when the present current value reaches a predetermined percentage of the initial current value.

25. The apparatus as defined in claim 24, wherein the supply of power to the energy applicator is terminated when the present current value is between about five and thirty percent of the initial current value.

26. The apparatus as defined in claim 19, wherein the second electrode is slidably adjustable with respect to the first electrode.

27. The apparatus as defined in claim 19, further comprising:
a timer that measures a preset period of time from activation of the energy applicator; and
circuitry for terminating supply of power to the energy applicator when the preset period elapses.

28. The apparatus as defined in claim 19, wherein the energy applicator contains a coding element, the apparatus further comprising circuitry that measures a value of a parameter of the coding element to determine an upper power or current limit value corresponding to a maximum power density or current density to be applied to the biological tissue.

29. The apparatus as defined in claim 19, wherein said applicator further comprises an expandable member having a contracted diameter for insertion into the biological tissue and an expanded diameter, the first electrode disposed on the expandable member.

30. The apparatus as defined in claim 29 wherein the energy applicator further comprises means for injecting a pressurizing fluid into the expandable member, the pressurizing fluid moderating the temperature of the first electrode.

31. A method for cauterizing a volume of biological tissue exhibiting a given shape and size comprising:

provim apparatus comprising an energy applicator having first and second electrodes disposed along a base having a longitudinal axis and exhibiting unique electrode parameters when activated, that provide a cauterization zone of current therebetween corresponding with said given size and shape of said volume of biological tissue;

determining the size and shape of said volume of biological tissue;

selecting the spacing along said axis between said first and second electrodes as a said unique electrode parameter to derive a said cauterization zone of current substantially encompassing and conforming with said determined size and shape of said volume of biological tissue;

coupling the energy applicator to a power source;

inserting the energy applicator into a location with respect to said volume of biological tissue effective to apply said zone of current substantially only thereto; and activating the energy applicator for a period of time to cauterize the volume of biological tissue.

32. The method as defined in claim 31, further comprising steps of:

detecting an initial current value of current supplied to said first and second electrodes of the energy applicator upon initial activation of the energy applicator;

detecting a present current value during continued activation of the first and second electrode of the energy applicator; and terminating supply of power to the energy applicator when the present current value reaches a predetermined percentage of the initial current value.

33. The method as defined in claim 31, further comprising steps of:

measuring a preset time period from initial activation of the first and second electrode of the energy applicator; and terminating supply of power to the first and second electrode of the energy applicator when the preset period of time elapses.

34. A method for cauterizing biological tissue comprising:

providing apparatus comprising a handle and a plurality of energy applicators, each one of the plurality of energy applicators having unique electrode parameters that provide cauterization of correspondingly different predetermined volumes of biological tissue;

determining the size and shape of an abnormal mass of biological tissue;

selecting an energy applicator having electrode parameters that provide cauterization of a predetermined volume of biological tissue suitable for cauterizing a volume the size and shape of the abnormal mass of biological tissue;

coupling the energy applicator to a power source;

inserting the energy applicator into the abnormal mass of biological tissue;

activating the energy applicator for a period of time to cauterize the abnormal mass of biological tissue; and wherein the step of selecting the electrode parameters includes selecting an energy applicator having at least a first electrode disposed upon an expandable member, the method further comprising, before the step of activating the energy applicator, a step of expanding the expandable member to increase a surface area of the electrode.

35. A method for cauterizing biological tissue comprising:

providing apparatus comprising a handle and a plurality of energy applicators, each one of the plurality of energy applicators having unique electrode parameters that provide cauterization of correspondingly different predetermined volumes of biological tissue;

determining the size and shape of an abnormal mass of biological tissue;

selecting an energy applicator having electrode parameters that provide cauterization of a predetermined volume of biological tissue suitable for cauterizing a volume the size and shape of the abnormal mass of biological tissue;

coupling the energy applicator to a power source;

inserting the energy applicator into the abnormal mass of biological tissue;

activating the energy applicator for a period of time to cauterize the abnormal mass of biological tissue; and further comprising steps of:

inserting an extraction device through the lumen and into the abnormal mass of biological tissue;

extending the energy applicator into the biological tissue to gather a tissue sample in the extraction device; and retrieving the extraction device through the lumen after the tissue sample has been gathered.

36. The method of claim 31 wherein said step of selecting the spacing between said first and second electrodes includes the step of selecting the surface areas thereof as a said unique electrode parameter.

* * * * *

UNITED STATES PATENT AND TRADEMARK OFFICE
CERTIFICATE OF CORRECTION

PATENT NO. : 6,312,428 B1
DATED : November 6, 2001
INVENTOR(S) : Philip E. Eggers and Ascher Shmulewitz Page 1 of 1

It is certified that error appears in the above-identified patent and that said Letters Patent is hereby corrected as shown below:

Title page,
Item [63], should read as follows:

-- [63] Continuation of application No. 08/887,663, filed on July 3, 1997, now Pat. No. 5,947,964, which is a continuation-in-part of application No. 08/842,009, filed April 23, 1997, now Pat. No. 5,928,159, which is a continuation of application No.08/398,644 filed March 3, 1995, now Pat. No. 5,630,426. --

Column 1,
Lines 8-15, should read as follows:
-- This application is a continuation of U.S. patent application Serial No. 08/887,663, filed on July 3, 1997, now Pat. No. 5,947,964, which is a continuation-in-part of U.S. patent application Serial No. 08/842,009, filed April 23, 1997, entitled APPARATUS AND METHOD FOR CHARACTERIZATION AND TREATMENT OF TUMORS, now Pat. No. 5,928,159, which is a continuation of U.S. patent application Serial No. 08/398,644 filed March 3, 1995, now Pat. No. 5,630,426. --

Signed and Sealed this

Twenty-ninth Day of June, 2004

JON W. DUDAS
*Acting Director of the United States Patent and Trademark Office*